(12) United States Patent
Sudin et al.

(10) Patent No.: US 10,918,834 B2
(45) Date of Patent: Feb. 16, 2021

(54) ROTATIONALLY TORQUABLE ENDOVASCULAR DEVICE WITH ACTUATABLE WORKING END

(71) Applicant: RAPID MEDICAL LTD., Yokneam (IL)

(72) Inventors: Yuri Sudin, Modiin (IL); Ronen Eckhouse, Shimshit (IL); Aharon Friedman, Haifa (IL); Matan Gedulter, Givat Ela (IL); Moshe Miller, Jerusalem (IL)

(73) Assignee: RAPID MEDICAL LTD., Yokneam (IL)

( * ) Notice: Subject to any disclaimer, the term of this patent is extended or adjusted under 35 U.S.C. 154(b) by 0 days.

(21) Appl. No.: 16/337,511

(22) PCT Filed: Sep. 28, 2017

(86) PCT No.: PCT/IB2017/001663
§ 371 (c)(1),
(2) Date: Mar. 28, 2019

(87) PCT Pub. No.: WO2018/060776
PCT Pub. Date: Apr. 5, 2018

(65) Prior Publication Data
US 2019/0224457 A1 Jul. 25, 2019

Related U.S. Application Data

(60) Provisional application No. 62/401,387, filed on Sep. 29, 2016.

(51) Int. Cl.
*A61M 25/01* (2006.01)
*A61M 25/09* (2006.01)
*A61B 17/00* (2006.01)

(52) U.S. Cl.
CPC ... *A61M 25/0147* (2013.01); *A61B 17/00234* (2013.01); *A61M 25/09025* (2013.01);
(Continued)

(58) Field of Classification Search
CPC ...... A61M 25/0147; A61M 2025/0681; A61M 25/09041; A61M 2025/09066;
(Continued)

(56) References Cited

U.S. PATENT DOCUMENTS

| 4,815,478 A | 3/1989 | Buchbinder et al. |
| 5,318,529 A | 6/1994 | Kontos |

(Continued)

FOREIGN PATENT DOCUMENTS

| EP | 2 812062 B1 | 7/2019 |
| JP | 2015/506777 A | 3/2015 |

(Continued)

OTHER PUBLICATIONS

International Search Report for International Application No. PCT/ 162017/001663, dated Jul. 10, 2018 (4 pages).
(Continued)

*Primary Examiner* — Patrick Fernandes
(74) *Attorney, Agent, or Firm* — Finnegan, Henderson, Farabow, Garrett & Dunner, LLP (57) ABSTRACT

An endovascular device including a hollow shaft having a proximal end and a distal end, and sized for insertion into a blood vessel, may be provided. The endovascular device may also include a control line configured to extend through the hollow shaft and an actuatable working portion situated distally from the distal end of the hollow shaft and configured to receive an actuation force transmitted via the control line. The endovascular device may further include an actuator configured to exert the actuation force on the control line to cause relative movement between the control line and the (Continued)

hollow shaft and to actuate the working portion. The endovascular device may also include a rotation restriction barrier configured to substantially impede the control line from rotating relative to the working portion, while permitting relative axial movement between the control line and the hollow shaft.

21 Claims, 6 Drawing Sheets

(52) U.S. Cl.
CPC . *A61M 25/09041* (2013.01); *A61B 2017/003* (2013.01); *A61B 2017/00323* (2013.01); *A61M 2025/09066* (2013.01)

(58) Field of Classification Search
CPC ... A62M 25/09025; A61B 2017/00292; A61B 2017/003; A61B 17/00234; A61B 2017/00323
See application file for complete search history.

(56) References Cited

U.S. PATENT DOCUMENTS

| | | | |
|---|---|---|---|
| 5,484,409 A | 1/1996 | Atkinson et al. | |
| 2004/0092845 A1* | 5/2004 | Gaber | A61M 25/09025 600/585 |
| 2007/0088323 A1 | 4/2007 | Campbell et al. | |
| 2009/0198219 A1 | 8/2009 | Campbell et al. | |
| 2010/0228150 A1* | 9/2010 | Zimmerman | A61M 25/09 600/585 |
| 2010/0249773 A1 | 9/2010 | Clark et al. | |
| 2014/0052109 A1 | 2/2014 | Organ et al. | |
| 2014/0350568 A1 | 11/2014 | Shekalim et al. | |
| 2016/0158497 A1* | 6/2016 | Tran | A61F 2/2436 623/2.11 |
| 2018/0229009 A1 | 8/2018 | Campbell et al. | |

FOREIGN PATENT DOCUMENTS

| | | |
|---|---|---|
| WO | WO 2013/118105 A1 | 8/2013 |
| WO | WO 2014/053918 A2 | 10/2014 |

OTHER PUBLICATIONS

Written Opinion of the International Searching Authority for International Application No. PCT/IB2017/001663, dated Jul. 10, 2018 (6 pages).

Extended Supplementary European Search Report, Application No. 17855084.4—1132/3518835—PCT/IB2017001663, dated May 18, 2020, (7 pages).

* cited by examiner

ROTATIONALLY TORQUABLE ENDOVASCULAR DEVICE WITH ACTUATABLE WORKING END

PRIORITY

This application is a U.S. national stage entry under 35 U.S.C. § 371 of International Application No. PCT/162017/001663, filed Sep. 28, 2017, which claims the benefit of priority from U.S. Provisional Application No. 62/401,387, filed Sep. 29, 2016, both of which are herein incorporated by reference in their entireties.

FIELD

This disclosure relates generally to endovascular devices.

SUMMARY

Endovascular devices may include a hollow elongated shaft connected to a working portion at its distal end, and an elongated control element which may be connected to a distal tip of the working portion. The control wire may be connected to a proximal actuator which can create a relative axial motion between the control wire and the working portion and the shaft. When the control wire is pulled by the actuator, for example, the distal tip of the working member is also pulled and a relative motion at the distal tip can be achieved. One example of such an endovascular device may include a wire mesh that expands when the control wire is pulled. Another example may include a guidewire tip which bends when the control wire is pulled.

An endovascular hollow shaft may be made in a number of different ways. For example, a hollow shaft may be made from a hollow metallic tube or a cable of wires. As another example, the hollow shaft may be made from layers of polymers such as polytetrafluoroethylene (PTFE) and PEBAX (available from Arkema) or with a combination of a reinforcement braid or coil and such polymers. As yet another example, an endovascular shaft may be made from a combination of any of the above. For example, the proximal 100 cm portion may be made from a metallic tube, then 30 cm of PTFE coated cable of wires can be bonded, and finally a single wire coil can be bonded to create a supple distal section.

The control wire may include several wires that collectively form a control cable. The control wire, for example, may be made of metal wires or materials, polymers or other materials. The control wires may also be made from a combination of the materials and components listed above, and may include different sections with different stiffness. In one example, the control wire may be made from a single wire which is grinded at its distal section to achieve flexibility of the wire.

The design of endovascular devices which incorporate a control wire, operate to help allow a physician to transfer a movement in a proximal actuator or handle to a distal working portion. The physician may control the handle outside of a patient's body with the working portion acting at a target location in the patient. While this design allows for the transmission of axial forces from the proximal handle to the distal working portion, because the elongated shaft is typically round and hollow and the control wire is hollow, it may be limited in its ability to transmit radial movement from the proximal to the distal end.

This limitation may be caused, for example, in view of the control wire and elongated shaft being connected only at the distal end. As a result, rotating the elongated shaft in its proximal part does not necessarily result in rotating of the control wire due to some of the radial torque transmitted to the shaft elastic deformation. In an exemplary endovascular device of the present disclosure, a fixture may enable transmission of the radial force of the elongated shaft to the control wire with a 1:1 ratio. This may be achieved, for example, by preventing the axial rotation between the control wire and the elongated shaft without preventing the axial movement between these two members.

Preventing axial rotation between the control wire and the elongated shaft without preventing the axial movement between these two members may be achieved, for example, by deforming at least a portion of the control wire and making at least a portion of the inner cross section of the round elongated shaft non-round, respectively. In accordance with exemplary embodiments of an endovascular device, there may be an overlap between the two rectangular portions even during axial movement of the control wire compare to the elongated shaft.

The disclosed embodiments may include an endovascular device including a hollow shaft having a proximal end and a distal end, and sized for insertion into a blood vessel. The endovascular device may also include a control line having a proximal end and a distal end, and extending through the hollow shaft. The endovascular device may also include an actuatable working portion located beyond the distal end of the hollow shaft, and configured to receive an actuation force transmitted via the distal end of the control line. The endovascular device may further include an actuator configured to exert the actuation force on the proximal end of the control line, to thereby cause relative movement between the control line and the hollow shaft and to actuate the working portion. The endovascular device may also include at least one control line rotation restrictor integral with the control line and located within the hollow shaft; and at least one rotation restrictor element associated with at least one of the hollow shaft and the working portion, and configured to engage with the control line rotation restrictor to thereby substantially impede the control line from rotating relative to the working portion, while permitting relative axial movement between the control line and the hollow shaft.

In another embodiment, the at least one control line rotation restrictor of the endovascular device includes at least one deformation of the control line. The at least one deformation may include at least one flattened portion of the control line.

In another embodiment, the control line of the endovascular device includes a region of round cross-section adjacent to the at least one deformation.

In another embodiment, the hollow shaft of the endovascular device may be formed of at least one wound wire.

In another embodiment, the hollow shaft of the endovascular device may include a cable formed of a plurality of wires.

In another embodiment, the working portion of the endovascular device includes a bendable tip formed of a coiled wire section beyond the distal end of the hollow shaft.

In another embodiment, the coiled wire section of the endovascular device has a flexibility greater than a flexibility of the hollow shaft.

In another embodiment, the actuator of the endovascular device includes a control handle configured to transmit at a ratio of approximately 1:1, rotational force exerted on the control handle to rotational force on the working portion.

In another embodiment, the at least one rotation restriction barrier of the endovascular device may include at least one deposit of material within at least one of the hollow shaft and the working portion, and wherein the deposit of material narrows a portion of a channel in at least one of the hollow shaft and the working portion. The deposited material may be a polymer.

In another embodiment, the at least one rotation restriction barrier of the endovascular device may include a first rotation restriction barrier in the hollow shaft and a second rotation restriction barrier in a channel of the working portion.

In another embodiment, the at least rotation restriction barrier of the endovascular device may include a first rotation restriction barrier in the hollow shaft and a second rotation restriction barrier in the coiled wire section.

In another embodiment, the control handle of the actuator is configured to enable pulling of the control line, to thereby cause the coiled section to bend and to transmit rotational torque to the bent coiled section when the control handle is rotated.

In another embodiment, the control line rotation restrictor and the rotation restriction barrier of the endovascular device may each have an axial length, such that when axially moved relative to each other, the control line rotation restrictor and the rotation restrictor element remain engaged.

In another embodiment, the endovascular device may be configured to permit a user to exert an applied relative rotational force of between the distal tip and a control line to the control handle, and the control line rotation restrictor and the rotation restriction barrier are configured to transmit the applied force to the working portion without substantial slippage between the control line rotation restrictor and the rotation restriction barrier.

In another embodiment, the hollow shaft of the endovascular device includes a hollow metallic tube and the working portion includes a coiled wire distal to the hollow metallic tube.

In another embodiment, the hollow shaft of the endovascular device includes a polymeric tube and the working portion includes a coiled wire distal to the polymeric tube.

In another embodiment, the control line of the endovascular device is formed of a single wire and wherein the at least one control line rotation restrictor includes at least one deformation in a cross-sectional area of the single wire.

In another embodiment, the at least one control line rotation restrictor of the endovascular device includes at least a first deformation in an elongated region of the control line within the hollow shaft, and at least a second deformation of the control line in an elongated region of the working portion.

BRIEF DESCRIPTION OF THE DRAWINGS

The accompanying drawings, which are incorporated in and constitute a part of this specification, illustrate disclosed embodiments and, together with the description, serve to explain the disclosed embodiments.

Annotations appearing in the figures are exemplary only, and are not restrictive of the invention as claimed.

DETAILED DESCRIPTION

Reference will now be made in detail to the present embodiments (exemplary embodiments) of the disclosure, examples of which are illustrated in the accompanying drawings.

Figure 1:
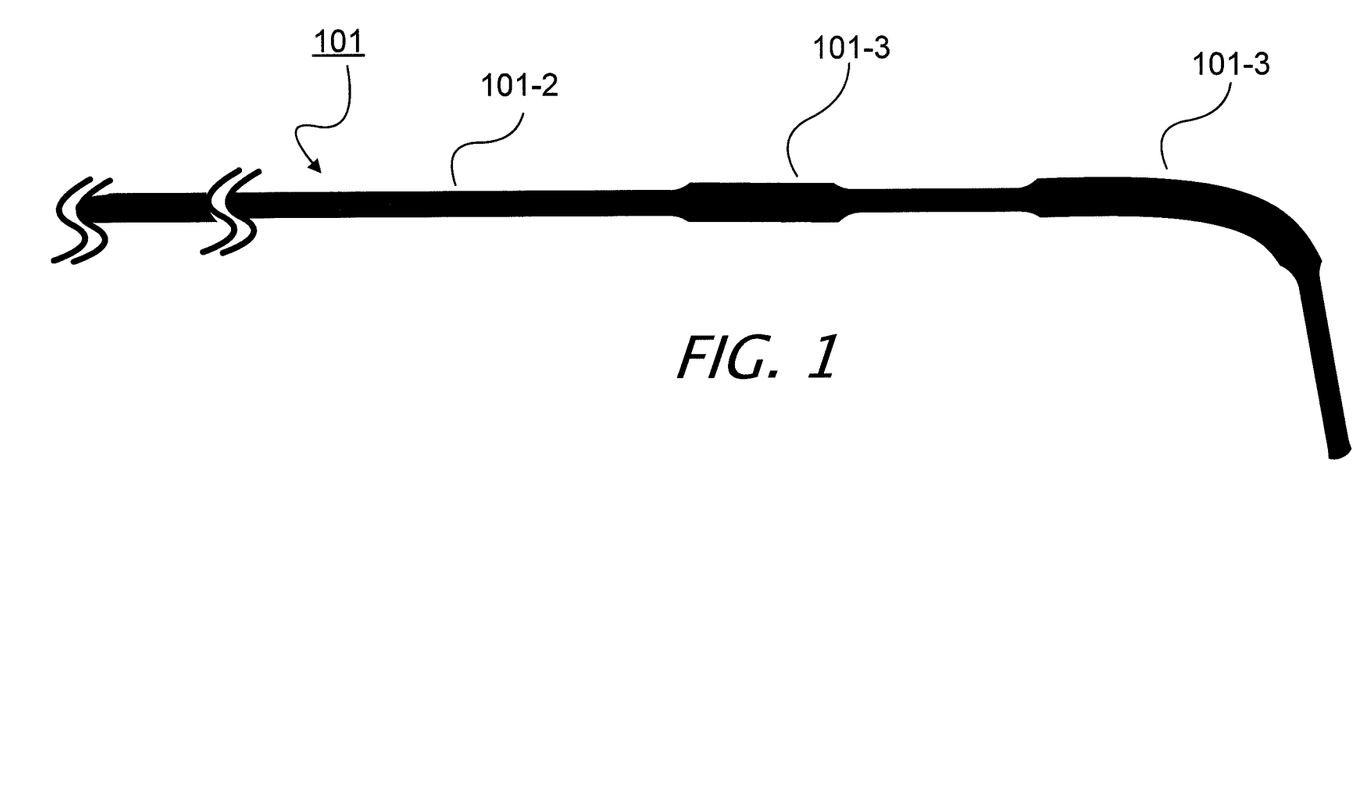
FIG. 1 is an illustration of a control wire for an exemplary endovascular device, consistent with at least one of the disclosed embodiments.
Figure 2:
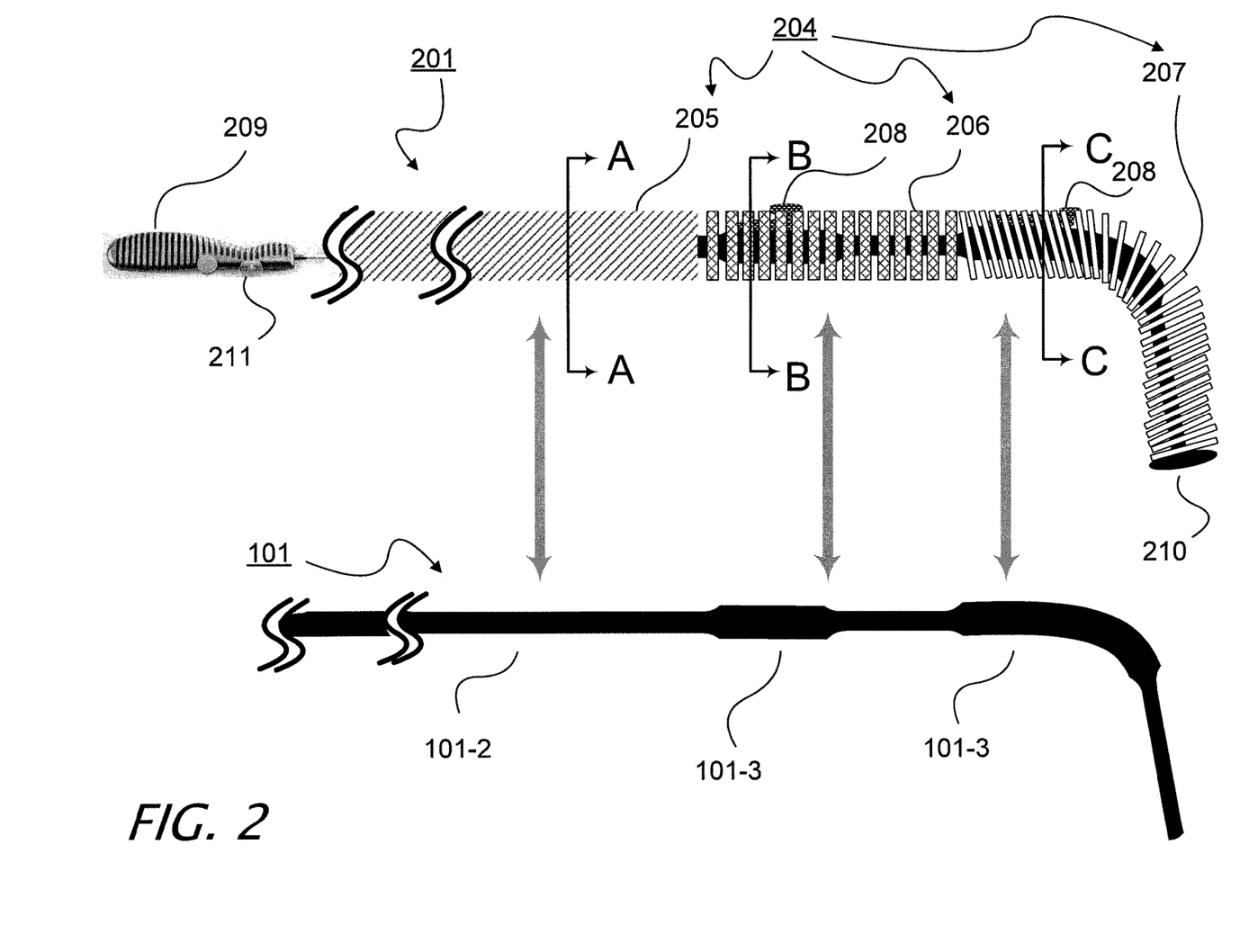
FIG. 2 is an illustration of an exemplary endovascular device with the control wire of FIG. 1, consistent with at least one of the disclosed embodiments.

FIG. 1 illustrates a control line 101 (e.g., a control wire) of an exemplary endovascular device in accordance with the disclosure, which may be deformed or flattened in two zones that form control line rotation restrictors 101-3, and may be round in other areas along its axis 101-2. FIG. 2 illustrates an exemplary endovascular device 201 using control line 101 in accordance with the disclosure. (Solely to illustrate the position of zone 101-2 and control line rotation restrictor 101-3 in endovascular device 201, with the understanding that control line 101 is part of endovascular device 201, FIG. 2 also separately depicts control line 101 of FIG. 1, with control line rotation restrictors 101-3 and zone 101-2 generally aligned to endovascular device 201.) As shown in FIG. 2, endovascular device 201 may also include an elongated shaft 204 which may include a tube 205, a cable of wires 206, and a working portion 207 (e.g., a single wire coil as shown in FIG. 2). A distal tip 210 of the elongated shaft 204 may be attached to control line 101, for example. At a proximal end of the elongated shaft 204, the control line 101 may be connected to a slider 211 of an actuator 209 (e.g., a handle as shown in FIG. 2), with the elongated shaft 204 connected to the actuator 209 to facilitate the relative movement. (In FIG. 2, actuator 209 is not depicted to the same scale as that of elongated shaft 204.) In accordance with at least some embodiments, two rotation restriction barriers 208 (e.g., polymers) may be inserted between the elongated shaft 204 and the control line 101 to prevent the radial movement between the control line 101 and the elongated shaft 204.

Figure 9:
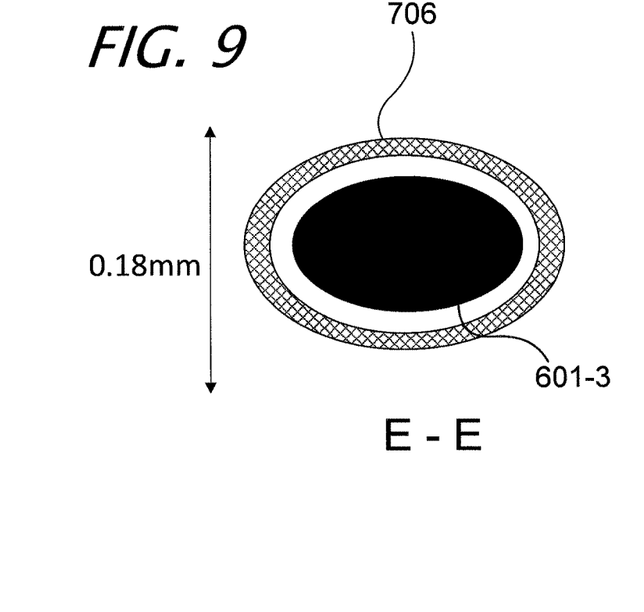
FIG. 9 is an illustration of an inner cross section of a section of the exemplary endovascular device of FIG. 7, consistent with at least one of the disclosed embodiments.
Figure 10:
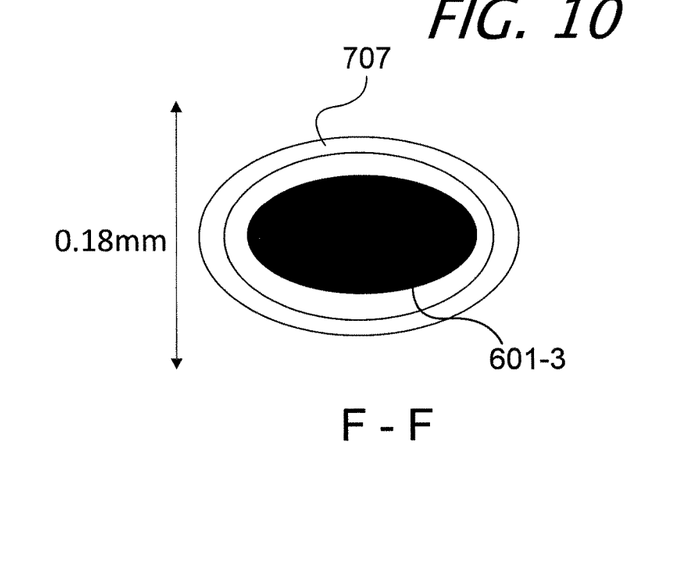
FIG. 10 is an illustration of an inner cross section of a section of the exemplary endovascular device of FIG. 7, consistent with at least one of the disclosed embodiments.

Consistent with the embodiment shown in FIGS. 9 and 10, in at least some embodiments of an exemplary endovascular device of the disclosure, the cable of wires 206 and the working portion 207 of the elongated shaft 204 may be elliptical. This elliptical shape resists relative rotation of the elongated shaft 204 and the control line 101, enabling torqueing of the device. Alternatively, other non-symmetrical shapes (e.g., cross-sections) may be employed, consistent with the invention to resist rotation and to permit torqueing.

At least some embodiments of an exemplary endovascular device of the disclosure may encompass a fixture enabling transmission of a radial force of the elongated shaft 204 to the control line 101 with 1:1 ratio. This may be achieved, for example, by preventing axial rotation between the control line 101 and the elongated shaft 204 without preventing the axial movement between the control line 101 and the elongated shaft 204. And such axial rotation prevention (without axial movement prevention) may be achieved, for example, by deforming at least a portion of the control line 101 and making at least a portion of the inner cross section of the round elongated shaft 204 non-round, respectively. For example, there may be an overlap between the two rectangular (or flattened) portions that form control line rotation restrictors 101-3 even during axial movement of the control line 101 compared to the elongated shaft 204.

A control line 101 with at least some flat or rectangular section or sections may be achieved by, for example, selectively pressing the control line 101, by adhesion of additional materials to form a non-round shape, or by other means.

Achieving a non-round inner cross section may be achieved, for example, by attaching rectangular shaped rotation restriction barriers 208 to an inner wall of the elongated shaft 204. As another example, a rotation restriction barriers 208 may include a polymer inserted through the wire cable to create a non-round cross section. The polymer of the rotation restriction barriers 208 may be heated and inserted through holes in the wall of the elongated shaft 204 and shaped as needed by a rectangular mandrel.

Figure 3:
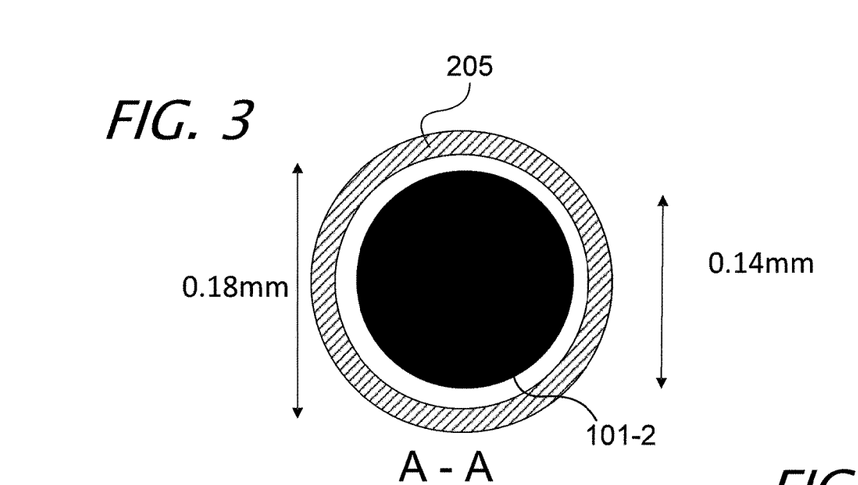
FIG. 3 is an illustration of an inner cross section of a section of the exemplary endovascular device of FIG. 2, consistent with at least one of the disclosed embodiments.

As shown in FIG. 3, which illustrates an inner cross section A-A of a section of exemplary endovascular device 201, the control line 101 may be made from 0.14 mm Nitinol wire. A distal tip of the control line 101 may be gradually grinded to an outer diameter of about 70 um. The elongated shaft 204 may be made from a 130 cm Nitinol tube with an inner diameter of 0.18 mm which may be bonded to a PTFE covered cable of ten 70 um Nitinol wires and the distal section may be a single 70 um wire which may be coiled.

Figure 4:
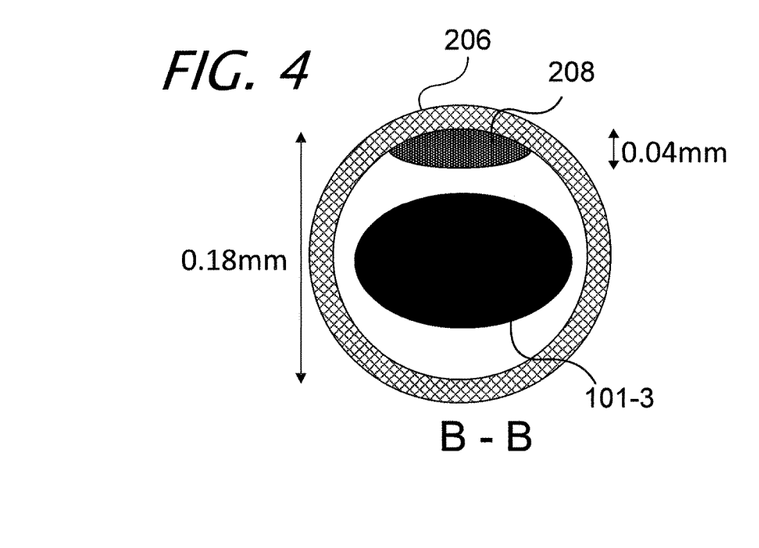
FIG. 4 is an illustration of an inner cross section of a section of the exemplary endovascular device of FIG. 2, consistent with at least one of the disclosed embodiments.

As shown in FIG. 4, which illustrates an inner cross section B-B of a section of exemplary endovascular device 201, the control line 101 may be pressed to create flat sections that form control line rotation restrictors 101-3 of about 0.16 mm×0.12 mm of 30 mm of length. Using a rectangular mandrel, a rotation restriction barrier 208 (e.g., a polymer) may be inserted through the wire cable 206 to create a non-round cross section in areas that overlap the non-round sections of the control line 101. As a result, relative axial movement between the control line 101 and the elongated shaft 204 may be maintained while the axial rotation between the control line 101 and the elongated shaft 204 (which includes cable 206) may be prevented.

Figure 5:
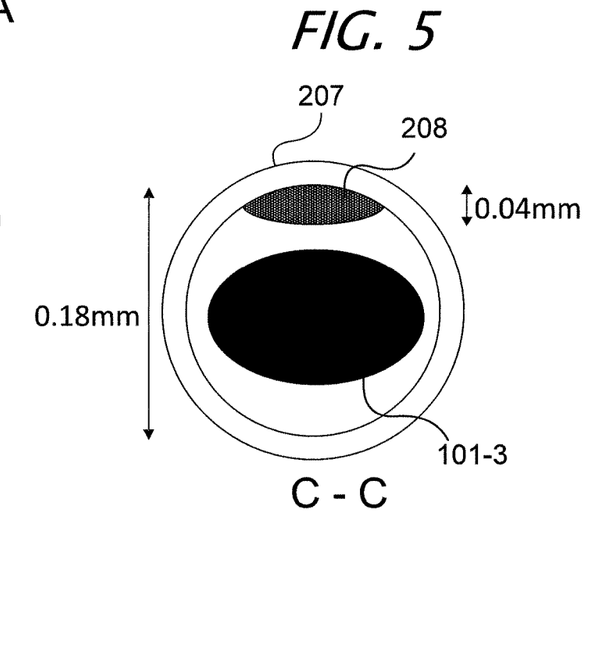
FIG. 5 is an illustration of an inner cross section of a section of the exemplary endovascular device of FIG. 2, consistent with at least one of the disclosed embodiments.

FIG. 5 illustrates an inner cross section C-C of a section of exemplary endovascular device 201, similar to cross section B-B of FIG. 4. Again, as a result, relative axial movement between the control line 101 and the elongated shaft 204 may be maintained while the axial rotation between the control line 101 and the elongated shaft 204 (which includes working portion 207) may be prevented.

Figure 6:
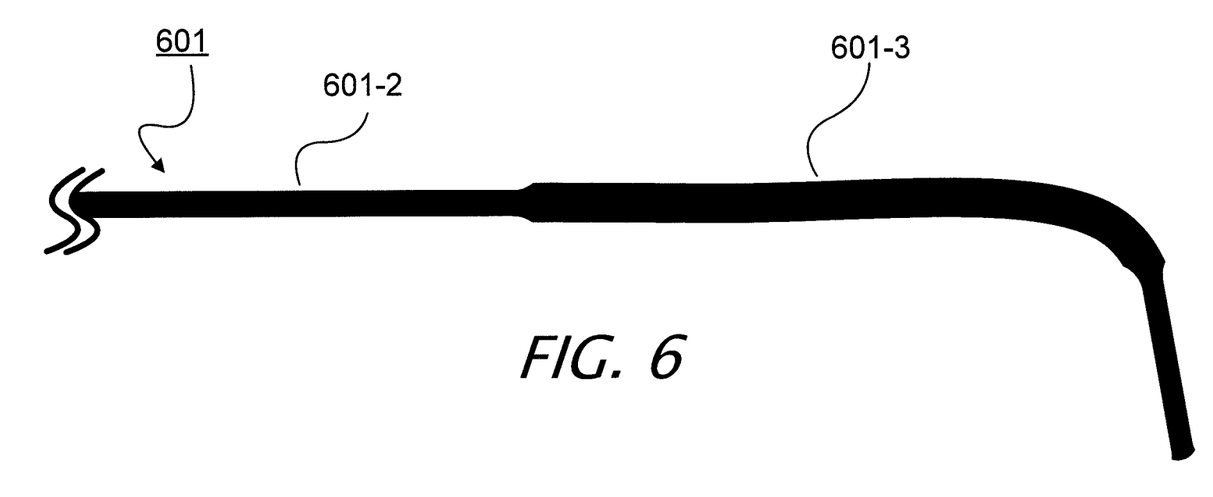
FIG. 6 is an illustration of a control wire for another exemplary endovascular device, consistent with at least one of the disclosed embodiments.
Figure 7:
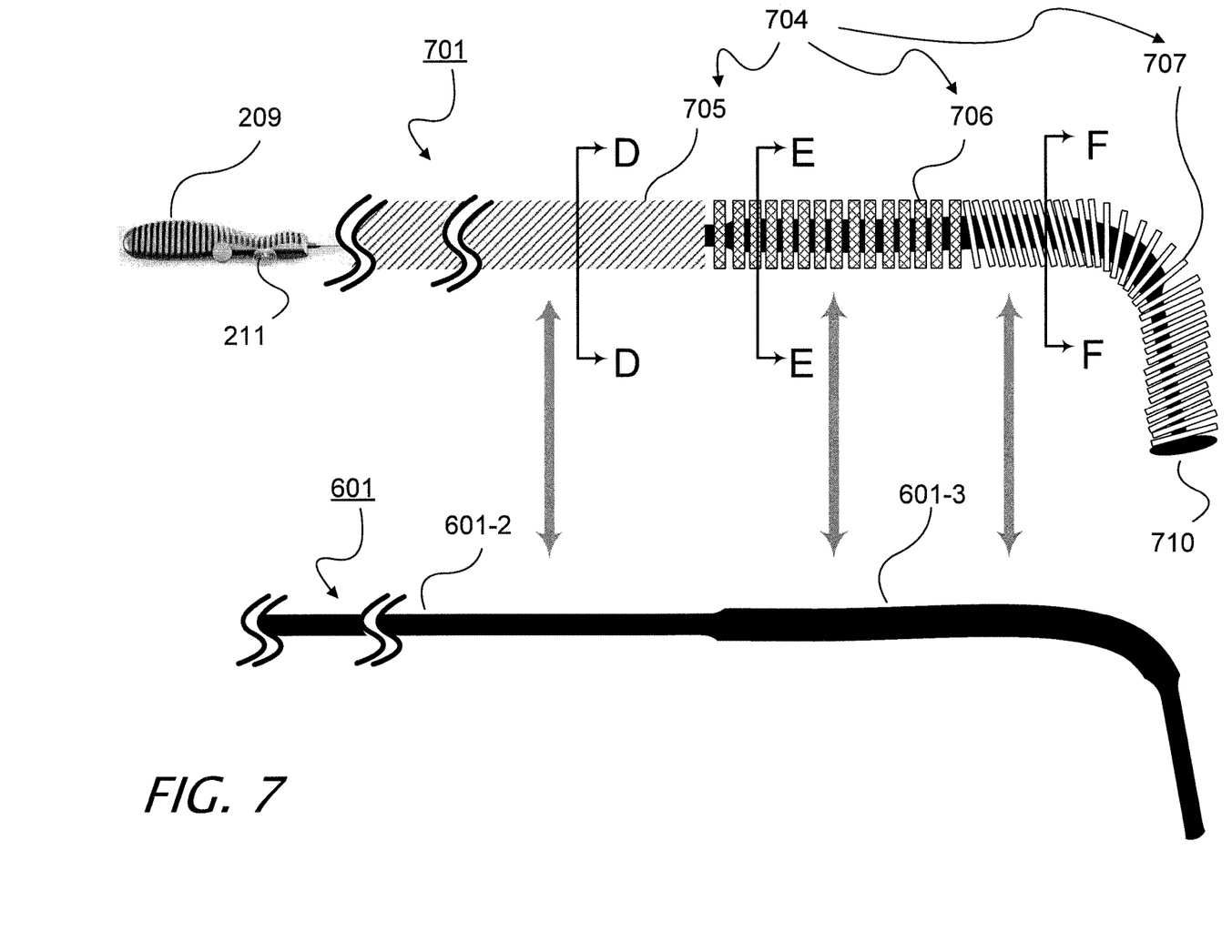
FIG. 7 is an illustration of an exemplary endovascular device with the control wire of FIG. 6, consistent with at least one of the disclosed embodiments.

In a further embodiment, FIG. 6 illustrates a control line 601 (e.g., a control wire) of an exemplary endovascular device in accordance with the disclosure, which may be deformed or flattened in a zone that forms control line rotation restrictor 601-3, and may be round in other areas along its axis 601-2. FIG. 7 illustrates an exemplary endovascular device 701 using control line 601 in accordance with the disclosure. (Solely to illustrate the position of zone 601-2 and control line rotation restrictor 601-3 in endovascular device 701, with the understanding that control line 601 is part of endovascular device 701, FIG. 7 also separately depicts control line 601 of FIG. 6, with control line rotation restrictor 601-3 and zone 601-2 generally aligned to endovascular device 701.) As shown in FIG. 7, endovascular device 701 may also include an elongated shaft 704 which may include a tube 705, a cable of wires 706, and a working portion 707 (e.g., a single wire coil as shown in FIG. 7). A distal tip 710 of the elongated shaft 704 may be attached to control line 601, for example. At a proximal end of the elongated shaft 704, the control line 601 may be connected to a slider 211 of an actuator 209, with the elongated shaft 704 connected to the actuator 209 to facilitate the relative movement. (In FIG. 7, actuator 209 is not depicted to the same scale as that of elongated shaft 704.)

Figure 8:
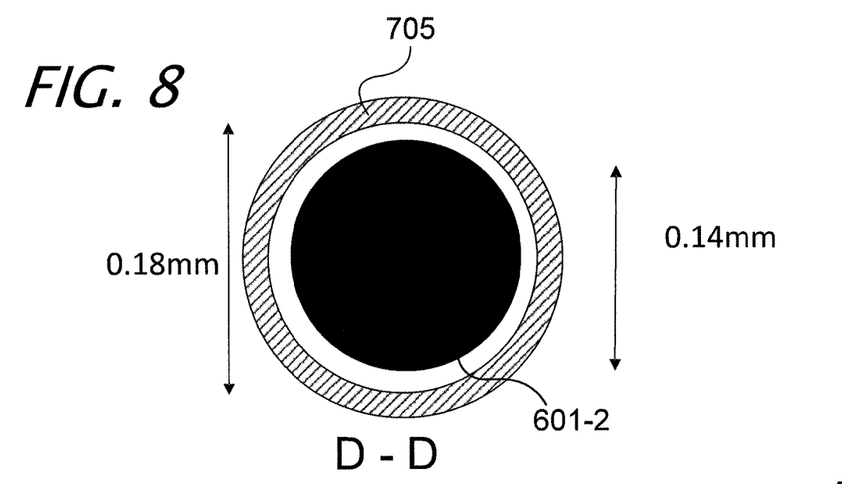
FIG. 8 is an illustration of an inner cross section of a section of the exemplary endovascular device of FIG. 7, consistent with at least one of the disclosed embodiments.

FIG. 8 illustrates an inner cross section D-D of a section of exemplary endovascular device 701. The control line 601 may be made from 0.14 mm Nitinol wire. A distal tip of the control line 601 may be gradually grinded to an outer diameter of about 70 um. The elongated shaft 704 may be made from a 130 cm Nitinol tube with an inner diameter of 0.18 mm which may be bonded to a PTFE covered cable of ten 70 um Nitinol wires and the distal section may be a single 70 um wire which may be coiled.

As shown in FIGS. 9 and 10, which illustrates inner cross sections E-E and F-F of a section of exemplary endovascular device 701, the control line 601 may be pressed to create flat sections that form control line rotation restrictors 101-3 of about 0.16 mm×0.12 mm of 30 mm of length. As mentioned above, in FIGS. 9 and 10, the cable of wires 706 and the working portion 707 of the elongated shaft 704 may be elliptical. This elliptical shape resists relative rotation of the elongated shaft 704 and the control line 601, enabling torqueing of the device; that is, the elliptical cable of wires 706 and working portion 707 may form a rotation restriction barrier in some embodiments. Alternatively, other non-symmetrical shapes (e.g., cross-sections) may be employed, consistent with the invention to resist rotation and to permit torqueing.

In other embodiments, a single wire coil may be provided, extending from a multi-wire cable with a control wire that runs through the core of both. This enables the control wire to steer the more flexible coiled end of the coil, without causing the multi-wire cable to appreciably bend.

Moreover, while illustrative embodiments have been described herein, the scope includes any and all embodiments having equivalent elements, modifications, omissions, combinations (e.g., of aspects across various embodiments), adaptations or alterations based on the present disclosure. The elements in the claims are to be interpreted broadly based on the language employed in the claims and not limited to examples described in the present specification or during the prosecution of the application, which examples are to be construed as non-exclusive. Further, the steps of the disclosed methods can be modified in any manner, including by reordering steps or inserting or deleting steps. It is intended, therefore, that the specification and examples be considered as example only, with a true scope and spirit being indicated by the following claims and their full scope of equivalents.

What is claimed is:

1. An endovascular device, comprising:
    a hollow shaft having a proximal end and a distal end, the hollow shaft being sized for insertion into a blood vessel;
    a control line having a proximal end and a distal end, the control line configured to extend through the hollow shaft;
    an actuatable working portion situated distally from the distal end of the hollow shaft, the actuatable working portion configured to receive an actuation force transmitted via the distal end of the control line;
    an actuator configured to exert the actuation force on the proximal end of the control line to thereby cause relative movement between the control line and the hollow shaft and to actuate the actuatable working portion;
    at least one control line rotation restrictor integral with the control line and configured to be located at least partially within the hollow shaft; and
    at least one rotation restriction barrier associated with at least one of the hollow shaft or the actuatable working portion, wherein the at least one rotation restriction barrier is configured to engage with the at least one control line rotation restrictor to substantially impede the control line from rotating relative to the actuatable working portion, while permitting relative axial movement between the control line and the hollow shaft.

2. The endovascular device of claim 1, wherein the at least one control line rotation restrictor includes at least one deformation of the control line.

3. The endovascular device of claim 2, wherein the at least one deformation includes at least one flattened portion of the control line.

4. The endovascular device of claim 3, wherein the control line includes a region of round cross-section adjacent to the at least one deformation.

5. The endovascular device of claim 1, wherein the hollow shaft is formed of at least one wound wire.

6. The endovascular device of claim 1, wherein the hollow shaft includes a cable formed of a plurality of wires.

7. The endovascular device of claim 1, wherein the actuatable working portion includes a bendable tip formed of a coiled wire section situated distally from the distal end of the hollow shaft.

8. The endovascular device of claim 7, wherein the coiled wire section is configured for greater flexibility than the hollow shaft.

9. The endovascular device of claim 1, wherein the actuator includes a control handle configured to transmit, at a ratio of approximately 1:1, rotational force exerted on the control handle to rotational force on the actuatable working portion.

10. The endovascular device of claim 1,
    wherein the at least one rotation restriction barrier includes at least one deposit of material within at least one of the hollow shaft or the actuatable working portion, and
    wherein the deposit of material narrows a portion of a channel in at least one of the hollow shaft or the actuatable working portion.

11. The endovascular device of claim 1, wherein the at least one rotation restriction barrier includes:
    a first rotation restriction barrier situated at least partially within the hollow shaft; and
    a second rotation restriction barrier situated at least partially within a channel of the actuatable working portion.

12. The endovascular device of claim 7, wherein the actuator is configured to enable pulling of the control line to cause the coiled wire section to bend into a bent configuration and to transmit rotational torque to the coiled wire section in the bent configuration when at least a portion of the actuator is rotated.

13. The endovascular device of claim 1, wherein the at least one control line rotation restrictor and the at least one rotation restriction barrier each have an axial length, such that when axially moved relative to each other, the at least one control line rotation restrictor and the at least one rotation restriction barrier are configured to remain engaged.

14. The endovascular device of claim 1, wherein when a relative rotational force is applied between a distal tip of the actuatable working portion and the control line, the at least one control line rotation restrictor and the at least one rotation restriction barrier are configured to transmit the relative rotational force to the actuatable working portion without substantial slippage between the at least one control line rotation restrictor and the at least one rotation restriction barrier.

15. The endovascular device of claim 1,
    wherein the hollow shaft includes a hollow tube formed of at least one of a metallic material or a polymer; and
    wherein the actuatable working portion includes a coiled wire situated distally from the hollow tube.

16. The endovascular device of claim 1,
    wherein the control line is formed of a single wire, and
    wherein the at least one control line rotation restrictor includes at least one deformation in a cross-sectional area of the single wire of the control line.

17. The endovascular device of claim 16, wherein the at least one control line rotation restrictor includes:
    at least a first deformation formed in an elongated region of the control line that extends within the hollow shaft; and
    at least a second deformation formed in a portion of the control line that extends in an elongated region of the actuatable working portion.

18. An endovascular device, comprising:
    a hollow shaft having a proximal end and a distal end, the hollow shaft being sized for insertion into a blood vessel and being formed of at least one wound wire arranged in a first winding configuration;
    an actuatable working portion situated distally from the distal end of the hollow shaft, the actuatable working portion being constructed of at least one wound wire arranged in a second winding configuration that is different from the first winding configuration;
    a control line having a proximal end and a distal end, the control line being configured to extend through the hollow shaft, wherein the distal end of the control line is connected to the actuatable working portion; and
    at least one rotation restriction barrier associated with at least one of the hollow shaft or the actuatable working portion, the at least one rotation restriction barrier being configured to substantially impede the control line from rotating relative to the actuatable working portion while permitting relative axial movement between the control line and the hollow shaft,
    wherein the actuatable working portion is configured for greater flexibility than the hollow shaft, and
    wherein the actuatable working portion and the hollow shaft are configured such that when a force is applied to the control line, the at least one wire of the actuatable working portion is configured to bend while the at least one wire of the hollow shaft is configured to resist bending.

19. The endovascular device of claim 18,
wherein the hollow shaft is formed of a plurality of wires arranged in a cable, and
wherein the actuatable working portion is formed of a single wire arranged in a coil.

20. The endovascular device of claim 19, wherein the single wire coil of the actuatable working portion is connected to and extends distally from the multi-wire cable of the hollow shaft.

21. The endovascular device of claim 18, wherein the at least one rotation restriction barrier is configured to engage with at least one control line rotation restrictor integral with the control line to substantially impede the control line from rotating relative to the actuatable working portion.

\* \* \* \* \*